(12) United States Patent
Chopra

(10) Patent No.: US 8,859,097 B2
(45) Date of Patent: Oct. 14, 2014

(54) PHOTOCHROMIC COMPOUNDS, COMPOSITIONS AND ARTICLES

(75) Inventor: Anu Chopra, Pittsburgh, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 300 days.

(21) Appl. No.: 13/253,188

(22) Filed: Oct. 5, 2011

(65) Prior Publication Data
US 2012/0183810 A1 Jul. 19, 2012

Related U.S. Application Data

(60) Provisional application No. 61/459,671, filed on Dec. 16, 2010.

(51) Int. Cl.
| | | |
|---|---|---|
| G03C 1/73 | (2006.01) | |
| C09K 9/02 | (2006.01) | |
| C07D 311/94 | (2006.01) | |

(52) U.S. Cl.
CPC .......... *G03C 1/73* (2013.01); *C09K 2211/1029* (2013.01); *C09K 2211/1011* (2013.01); *C09K 2211/1088* (2013.01); *C09K 2211/1007* (2013.01); *C07D 311/94* (2013.01); *C09K 9/02* (2013.01); *Y10S 428/913* (2013.01)
USPC ........ 428/411.1; 428/412; 428/913; 524/110; 549/382

(58) Field of Classification Search
None
See application file for complete search history.

(56) References Cited

U.S. PATENT DOCUMENTS

| | | | |
|---|---|---|---|
| 5,645,767 A | 7/1997 | Van Gemert | |
| 6,025,026 A | 2/2000 | Smith et al. | |
| 6,068,797 A | 5/2000 | Hunt | |
| 6,113,814 A | 9/2000 | Gemert et al. | |
| 6,150,430 A | 11/2000 | Walters et al. | |
| 655,028 A1 | 4/2003 | Walters et al. | |
| 2003/0165686 A1 | 9/2003 | Blackburn et al. | |
| 2004/0191520 A1 | 9/2004 | Kumar et al. | |
| 2005/0151926 A1 | 7/2005 | Kumar et al. | |

FOREIGN PATENT DOCUMENTS

| | | |
|---|---|---|
| EP | 1184379 A1 | 3/2002 |
| WO | 0119813 A1 | 3/2001 |

OTHER PUBLICATIONS

Lange's Handbook of Chemistry, 15th ed. J.A. Dean, editor, McGraw Hill, 1999, pp. 9.1-9.8.

*Primary Examiner* — Ramsey Zacharia
(74) *Attorney, Agent, or Firm* — The Webb Law Firm

(57) ABSTRACT

The present invention provides a compound represented by the Formula I:

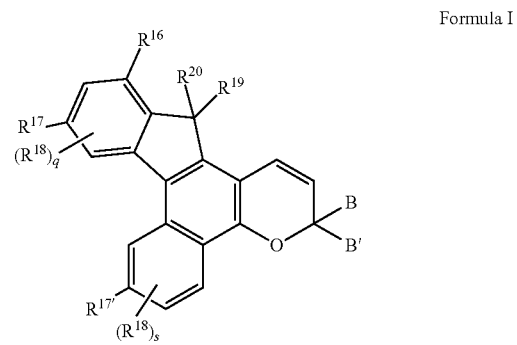

Formula I wherein substituents $R^{16}$ and $R^{17'}$ are each independently selected from an electron withdrawing group have a Hammett $\sigma_p$ value of from 0.05 to 0.85 and R17 is hydrogen.

26 Claims, No Drawings

PHOTOCHROMIC COMPOUNDS, COMPOSITIONS AND ARTICLES

CROSS REFERENCE TO RELATED APPLICATIONS

This application claims the benefit of priority of U.S. Provisional Patent Application No. 61/459,671, filed Dec. 16, 2010, all of which document is hereby incorporated herein by reference.

FIELD OF THE INVENTION

The present invention is directed to naphthopyran compounds, specifically indeno-fused naphthopyran compounds, such as photochromic indeno-fused naphthopyran compounds, having electron with drawing groups at specified positions.

BACKGROUND OF THE INVENTION

Many conventional photochromic materials, such as, for example, photochromic naphthopyrans, can undergo a transformation from a first form or state to a second form or state in response to the absorption of electromagnetic radiation. For example, many conventional thermally reversible photochromic materials are capable of transforming between a first "clear" or "bleached" ground-state form and a second "colored" activated-state form in response to the absorption of certain wavelengths of electromagnetic radiation (or "actinic radiation"). As used herein with reference to photochromic materials, articles and compositions, the terms "clear" and "bleached" mean the photochromic material, article, or composition is substantially without color, that is, has substantially no absorption of electromagnetic radiation within the visible region of the electromagnetic spectrum (420 nm-700 nm). As used herein the term "actinic radiation" refers to electromagnetic radiation that is capable of causing a photochromic material to transform from a first form or state to a second form or state. The photochromic material may then revert back to the clear ground-state form in response to thermal energy in the absence of actinic radiation. Photochromic articles and compositions that contain one or more photochromic materials, for example, photochromic lenses for eyewear applications, generally display optically clear and colored states that correspond to the photochromic material(s) that they contain. Thus, for example, eyewear lenses that contain photochromic materials can transform from a clear state to a colored state upon exposure to actinic radiation, such as certain wavelengths found in sunlight, and can revert back to the clear state in the absence of such radiation upon absorption of thermal energy.

When utilized in photochromic articles and compositions, conventional photochromic materials are typically incorporated into a host polymer matrix by one of imbibing, blending, and/or bonding. Alternatively, the photochromic material may be imbibed into a pre-formed article or coating. As used herein, the term "photochromic composition" refers to a photochromic material in combination with one or more other material, which may or may not be a different photochromic material.

For many photochromic applications, it is generally desirable to have a photochromic material that can rapidly revert from the colored, activated-state form to the clear, ground-state form, while still maintaining acceptable characteristics such as color density. For example, in photochromic eyewear applications, optical lenses comprising photochromic materials transform from an optically clear state to a colored state as the wearer moves from a region of low actinic radiation, such as indoors, to a region of high actinic radiation, such as into direct sunlight. As the lenses become colored, less electromagnetic radiation from the visible and/or ultraviolet regions of the electromagnetic spectrum is transmitted through the lens to the wearer's eyes. In other words, more electromagnetic radiation is absorbed by the lens in the colored state than in the optically clear state. When the wearer subsequently moves from the region of high actinic radiation back to a region of low actinic radiation, the photochromic material in the eyewear reverts from the colored, activated-state form to the clear, ground-state form in response to thermal energy. If this transformation from colored to clear takes several minutes or more, the wearer's vision may be less than optimal during this time due to the combined effect of the lower ambient light and the reduced transmission of visible light through the colored lenses.

Accordingly, for certain applications, it may be advantageous to develop photochromic materials that can more quickly transition from the colored form to the clear form, as compared to conventional photochromic materials. As used herein, the term "fade rate" is a measurement of the rate at which the photochromic material transforms from the activated colored state to the unactivated clear state. The fade rate for a photochromic material may be measured, for example, by activating a photochromic material to saturation under controlled conditions in a given matrix, measuring its activated steady state absorbance (i.e., saturated optical density) and then determining the length of time it takes for the absorbance of the photochromic material to decrease to one-half the activated steady state absorbance value. As measured in this fashion, the fade rate is designated by $T_{1/2}$, with units of seconds.

Additionally, as mentioned above, typically the transformation between the ground-state form and the activated-state form requires that the photochromic material be exposed to certain wavelengths of actinic radiation. For many conventional photochromic materials, the wavelengths of actinic radiation that may cause this transformation typically range from 320 nanometers ("nm") to 390 nm. Accordingly, conventional photochromic materials may not be optimal for use in applications that are shielded from a substantial amount of actinic radiation in the range of 320 nm to 390 nm. Therefore, for some applications, it may be advantageous to develop photochromic materials that can have a ground-state form absorption spectrum for electromagnetic radiation that is bathochromically shifted. As used herein, the term "bathochromically shifted" means having an absorption spectrum for electromagnetic radiation that is shifted to longer wavelength values. Thus a photochromic material that has a bathochromically shifted ground-state form absorption spectrum will require absorption of actinic radiation having a longer wavelength in order to transition from the ground-state form to the activated-state form.

For example, lenses for eyewear applications that are made using conventional photochromic materials may not reach their fully-colored activated-state form when used in an automobile. This is because a large portion of electromagnetic radiation in the range of 320 nm to 390 nm can be absorbed by the windshield of the automobile before it can be absorbed by the photochromic material(s) in the lenses. In certain applications, such as those involving behind the windshield use of photochromic materials, it may be advantageous if the ground-state form absorption spectrum of the photochromic material were bathochromically shifted such that the photochromic material may absorb sufficient electromagnetic radiation having a wavelength greater than 390 nm to permit the photochromic material to transform from the ground-state form to the activated-state form.

The absorption spectrum of a photochromic material in the activated-state form will correspond to the color of the medium or article containing the photochromic material, for example, the color of the eyewear lens, when exposed to actinic radiation. As specific wavelengths within the visible region of electromagnetic radiation are absorbed by a photochromic material in the activated-state form, the wavelengths within the visible region that are transmitted (i.e., not absorbed) correspond to the color of the photochromic material in the activated-state form. For example, absorption of wavelengths of light around about 500 nm to about 520 nm in the visible region of the electromagnetic spectrum results in a photochromic material that exhibits a "reddish" color, i.e., it absorbs visible radiation from the short wavelength or blue end of the visible spectrum and transmits radiation from the longer wavelength or red end of the visible spectrum. Conversely, absorption of wavelengths of light around about 580 nm to about 610 nm in the visible region of the electromagnetic spectrum results in a photochromic material that exhibits a "bluer" color, i.e., it absorbs visible radiation from the longer wavelength or red end of the visible spectrum and transmits radiation from the shorter wavelength or blue end of the visible spectrum.

Many current photochromic compounds have activated-state absorption spectrums that absorb visible light toward the blue end of the visible spectrum and exhibit a reddish color in the activated form. If the photochromic material has an activated-state absorption spectrum that is bathochromically shifted, i.e., shifted to absorb light having a longer wavelength, the photochromic material will exhibit a bluer color than the current photochromic material. For certain applications it may be desirable to have a photochromic material that has a bathochromically shifted activated form absorption spectrum for actinic radiation and which may therefore exhibit a bluer color.

SUMMARY OF THE INVENTION

The present invention is directed to a compound, such as a photochromic compound, represented by the following Formula I:

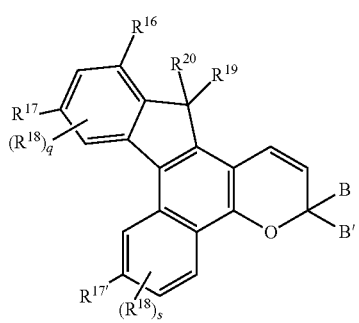

Formula I

In Formula I, $R^{16}$, $R^{17}$ and $R^{17'}$ are each independently selected from an electron withdrawing group having a Hammett $\sigma_p$ value of from 0.05 to 0.85, provided that one of $R^{16}$ and $R^{17}$ is hydrogen.

The substituent $R^{18}$ of Formula I is independently for each occurrence: hydrogen; halogen; $C_1$-$C_6$ alkyl; $C_3$-$C_7$ cycloalkyl; substituted or unsubstituted phenyl; $OR^{29}$ or —OC(=O)$R^{29}$, wherein $R^{29}$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$) alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and the phenyl substituents are $C_1$-$C_6$ alkyl or $C_1$-$C_6$ alkoxy; a mono-substituted phenyl, the phenyl having a substituent located at the para position, wherein the substituent at the para position is: a dicarboxylic acid residue, a diamine residue, an amino alcohol residue, a polyol residue, —CH$_2$—, —(CH$_2$)$_t$—, or —[O—(CH$_2$)$_t$]$_k$—, wherein t is the integer 2, 3, 4, 5 or 6 and k is an integer from 1 to 50, the substituent being connected to an aryl group on another photochromic material; —N($R^{30}$)$R^{31}$, wherein $R^{30}$ and $R^{31}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or ($C_1$-$C_6$)alkoxy($C_1$-$C_6$)alkyl, wherein said aryl group is phenyl or naphthyl, or $R^{30}$ and $R^{31}$ come together with the nitrogen atom to form a $C_3$-$C_{20}$ hetero-bicycloalkyl ring or a $C_4$-$C_{20}$ hetero-tricycloalkyl ring; a nitrogen containing ring represented by the following graphic formula IVA:

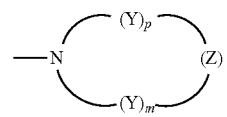

IVA wherein each —Y— is independently chosen for each occurrence from —CH$_2$—, —CH($R^{32}$)—, —C($R^{32}$)$_2$—, —CH(aryl)-, —C(aryl)$_2$-, and —C($R^{32}$)(aryl)-, and Z is —Y—, —O—, —S—, —S(O)—, —SO$_2$—, —NH—, —N($R^{32}$)—, or —N(aryl)-, wherein each $R^{32}$ is independently $C_1$-$C_6$ alkyl or hydroxy($C_1$-$C_6$)alkyl, each aryl is independently phenyl or naphthyl, m is an integer 1, 2 or 3, and p is an integer 0, 1, 2, or 3 and when p is 0, Z is —Y—; a group represented by one of the following graphic formulae IVB or IVC:

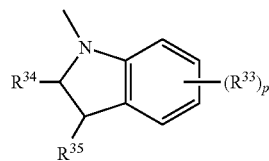

IVB

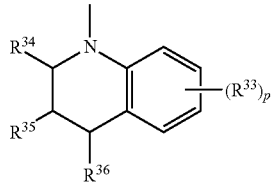

IVC wherein $R^{34}$, $R^{35}$, and $R^{36}$ are each independently hydrogen, $C_1$-$C_6$ alkyl, phenyl, or naphthyl, or the groups $R^{34}$ and $R^{35}$ together form a ring of 5 to 8 carbon atoms and each $R^{33}$ is independently for each occurrence from $C_1$-$C_6$ alkyl, $C_1$-$C_6$ alkoxy, or halogen and p is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_6$) alkyl;

Also, q is an integer from 0 to 2; and s is an integer from 0 to 3.

The substituents $R^{19}$ and $R^{20}$ are each independently; hydrogen; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W is hydrogen, hydroxy, $C_1$-$C_6$ alkyl, $C_1$-$C_6$ alkoxy, the unsubstituted, mono- or di-substituted aryl groups phenyl or naphthyl, phenoxy, mono- or di-($C_1$-$C_6$)alkoxy substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; —$OR^{37}$, wherein $R^{37}$ is $C_1$-$C_6$ alkyl, phenyl($C_1$-$C_3$)alkyl, mono($C_1$-$C_6$)alkyl substituted phenyl($C_1$-$C_3$)alkyl, mono ($C_1$-$C_6$)alkoxy substituted phenyl($C_1$-$C_3$)alkyl, $C_1$-$C_6$ alkoxy ($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group —CH($R^{38}$)Y", wherein $R^{38}$ is hydrogen or $C_1$-$C_3$ alkyl and Y" is CN, $CF_3$, or $COOR^{39}$, wherein $R^{39}$ is hydrogen or $C_1$-$C_3$ alkyl, or $R^{37}$ is the group, —C(=O)W', wherein W' is hydrogen, $C_1$-$C_6$ alkyl, $C_1$-$C_6$ alkoxy, the unsubstituted, mono- or di-substituted aryl groups phenyl or naphthyl, phenoxy, mono-, or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, or naphthyl group substituents are independently $C_1$-$C_6$ alkyl or $C_1$-$C_6$ alkoxy; or a mono-substituted phenyl, said phenyl having a substituent located at the para position, wherein the substituent is: a dicarboxylic acid residue, a diamine residue, an amino alcohol residue, a polyol residue, —$CH_2$—, —$(CH_2)_t$—, or —[O—$(CH_2)_t]_k$—, wherein t is from an integer 2, 3, 4, 5 or 6 and k is an integer from 1 to 50, the substituent being connected to an aryl group on another photochromic material; or $R^{19}$ and $R^{20}$ together form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings.

The substituents B and B' are each independently: an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently: hydroxyl, a group —C(=O)$R^{40}$, wherein $R^{40}$ is —$OR^{41}$, —N($R^{42}$)$R^{43}$, piperidino, or morpholino, wherein $R^{41}$ is allyl, $C_1$-$C_6$ alkyl, phenyl, mono($C_1$-$C_6$)alkyl substituted phenyl, mono($C_1$-$C_6$)alkoxy substituted phenyl, phenyl ($C_1$-$C_3$)alkyl, mono($C_1$-$C_6$)alkyl substituted phenyl($C_1$-$C_3$) alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, said halo substituent is chloro, fluoro, bromo or iodo, $R^{42}$ and $R^{43}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —[O—$(CH_2)_t]_k$—, wherein t is an integer 2, 3, 4, 5 or 6 and k is an integer from 1 to 50, the substituent being connected to an aryl group on another photochromic material: a croup represented by one of:

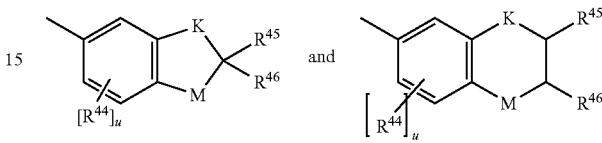

wherein K is —$CH_2$— or —O—, and M is —O— or substituted nitrogen, provided that when M is substituted nitrogen, K is the substituted nitrogen substituents being hydrogen, $C_1$-$C_{12}$ alkyl, or $C_1$-$C_{12}$ acyl, each $R^{44}$ being independently chosen for each occurrence from $C_1$-$C_{12}$ alkyl, $C_1$-$C_{12}$ alkoxy, hydroxy, and halogen, $R^{45}$ and $R^{46}$ each being independently hydrogen or $C_1$-$C_{12}$ alkyl, and u is an integer ranging from 0 to 2; or a

wherein $R^{47}$ is hydrogen or $C_1$-$C_{12}$ alkyl, and $R^{48}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen. Additionally, B and B' taken together can form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen.

The present invention also is directed to a photochromic composition comprising the previously described compound and, optionally, at least one other photochromic compound. The composition comprises:

(a) a single photochromic compound;
(b) a mixture of photochromic compounds;
(c) a material comprising at least one photochromic compound;
(d) a material to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

Additionally, the present invention provides a photochromic article comprising a substrate and the previously described photochromic compound connected to at least a portion of a substrate.

DETAILED DESCRIPTION OF THE INVENTION

As used in this specification and the appended claims, the articles "a," "an," and "the" include plural referents unless expressly and unequivocally limited to one referent.

Also, for the purposes of this specification and the claims, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

As mentioned above, the present invention is directed to a compound, such as a photochromic compound, represented by the following Formula I:

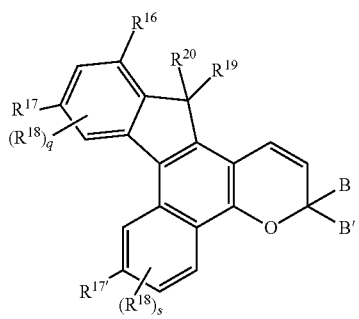

Formula I

In Formula I, $R^{16}$, $R^{17}$ and $R^{17'}$ are each independently selected from an electron withdrawing group having a Hammett $\sigma_p$ value of from 0.05 to 0.85, provided that one of $R^{16}$ and $R^{17}$ is hydrogen. Subject to the proviso, in a particular embodiment of the present invention, $R^{16}$, $R^{17}$ and $R^{17'}$ are each independently selected from fluoro, chloro, bromo, haloalkyl, haloalkoxy, cyano, nitro, sulfonyl, sulfonate, —OC(=O)$R^0$, or —C(=O)—X, wherein X is hydrogen, $C_1$-$C_6$ alkyl, —O$R^1$ or —N$R^2R^3$, wherein $R^0$, $R^1$, $R^2$ and $R^3$ are each independently hydrogen, $C_1$-$C_6$ alkyl, $C_5$-$C_7$ cycloalkyl, phenyl, mono-substituted phenyl, disubstituted phenyl, alkylene glycol, or polyalkylene glycol, wherein said mono- and disubstituted phenyl substituents are $C_1$-$C_6$ alkyl or $C_1$-$C_6$ alkoxy. Typically, (subject to the above-stated provision) $R^{16}$, $R^{17}$ and $R^{17'}$ are each independently selected from hydrogen, $C_1$-$C_4$ haloalkyl, chloro, fluoro, cyano, nitro, —OC(=O)$R^0$ or —C(=O)—X, wherein X is —O$R^1$ wherein $R^0$ and $R^1$ are each independently $C_1$-$C_4$ alkyl. More specifically, $R^{16}$, $R^{17}$ and $R^{17'}$ each independently can be selected from $CF_3$, $CF_2CF_3$, chloro, fluoro, cyano, nitro, acetyl, propionyl, methoxycarbonyl, and ethoxycarbonyl. Further, each of $R^{16}$ or $R^{17}$ can be hydrogen.

The substituent $R^{18}$ of Formula I is independently for each occurrence: hydrogen; halogen; $C_1$-$C_6$ alkyl; $C_3$-$C_7$ cycloalkyl; substituted or unsubstituted phenyl; —O$R^{29}$ or —OC(=O)$R^{29}$, wherein $R^{29}$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and the phenyl substituents are $C_1$-$C_6$ alkyl or $C_1$-$C_6$ alkoxy; a monosubstituted phenyl, the phenyl having a substituent located at the para position, wherein the substituent at the para position is: a dicarboxylic acid residue, a diamine residue, an amino alcohol residue, a polyol residue, —$CH_2$—, —$(CH_2)_t$—, or —[O—$(CH_2)_t]_k$—, wherein t is the integer 2, 3, 4, 5 or 6 and k is an integer from 1 to 50, the substituent being connected to an aryl group on another photochromic material; —N($R^{30}$)$R^{31}$, wherein $R^{30}$ and $R^{31}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or ($C_1$-$C_6$-)alkoxy($C_1$-$C_6$)alkyl, wherein said aryl group is phenyl or naphthyl, or $R^{30}$ and $R^{31}$ come together with the nitrogen atom to form a $C_3$-$C_{20}$ hetero-bicycloalkyl ring or a $C_4$-$C_{20}$ hetero-tricycloalkyl ring; a nitrogen containing ring represented by the following graphic

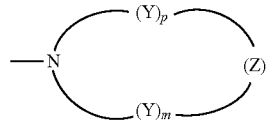

IVA wherein each —Y— is independently chosen for each occurrence from —$CH_2$—, —CH($R^{32}$)—, —C($R^{32}$)$_2$—, —CH(aryl)-, —C(aryl)$_2$-, and —C($R^{32}$)(aryl)-, and Z is —Y—, —O—, —S—, —S(O)—, —$SO_2$—, —NH—, —N($R^{32}$)—, or —N(aryl)-, wherein each $R^{32}$ is independently $C_1$-$C_6$ alkyl or hydroxy($C_1$-$C_6$)alkyl, each aryl is independently phenyl or naphthyl, m is an integer 1, 2 or 3, and p is an integer 0, 1, 2, or 3 and when p is 0, Z is —Y—; a group represented by one of the following graphic formulae IVB or IVC:

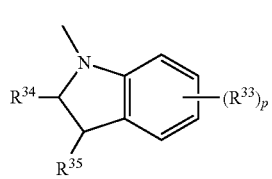

IVB

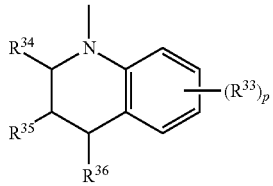

IVC wherein $R^{34}$, $R^{35}$, and $R^{36}$ are each independently hydrogen, $C_1$-$C_6$ alkyl, phenyl, or naphthyl, or the groups $R^{34}$ and $R^{35}$ together form a ring of 5 to 8 carbon atoms and each $R^{33}$ is independently for each occurrence from $C_1$-$C_6$ alkyl, $C_1$-$C_6$ alkoxy, or halogen and p is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_6$) alkyl.

Also, in a particular embodiment with reference to the compound of Formula I, $R^{18}$ for each occurrence is independently selected from $C_1$-$C_6$ alkyl, substituted $C_1$-$C_6$ alkyl, bromo, chloro, fluoro, phenyl, substituted phenyl, benzyl, substituted benzyl, $C_1$-$C_6$ alkoxy, $C_1$-$C_6$ perhaloalkyl, and amino. The substituent $R^{18}$ for each occurrence independently can be selected from hydrogen, $C_1$-$C_4$ alkyl, substituted $C_1$-$C_4$ alkyl, bromo, chloro, fluoro, phenyl, benzyl, $C_1$-$C_4$ alkoxy, $C_1$-$C_4$ haloalkyl, and amino. For example, $R^{18}$ for each occurrence independently can be selected from hydrogen, methyl, ethyl, bromo, chloro, fluoro, methoxy, ethoxy and $CF_3$.

With respect to Formula I, q is an integer from 0 to 2; and s is an integer from 0 to 3.

The substituents $R^{19}$ and $R^{20}$ are each independently: hydrogen; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W is hydrogen, hydroxy, $C_1$-$C_6$ alkyl, $C_1$-$C_6$ alkoxy, the unsubstituted, mono- or di-substituted aryl groups phenyl or naphthyl, phenoxy, mono- or di-($C_1$-$C_6$)alkoxy substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; —$OR^{37}$, wherein $R^{37}$ is $C_1$-$C_6$ alkyl, phenyl($C_1$-$C_3$)alkyl, mono($C_1$-$C_6$)alkyl substituted phenyl($C_1$-$C_3$)alkyl, mono ($C_1$-$C_6$)alkoxy substituted phenyl($C_1$-$C_3$)alkyl, $C_1$-$C_6$ alkoxy ($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group —CH($R^{38}$)Y", wherein $R^{38}$ is hydrogen or $C_1$-$C_3$ alkyl and Y" is CN, $CF_3$, or $COOR^{39}$, wherein $R^{39}$ is hydrogen or $C_1$-$C_3$ alkyl, or $R^{37}$ is the group, —C(=O)W', wherein W' is hydrogen, $C_1$-$C_6$ alkyl, $C_1$-$C_6$ alkoxy, the unsubstituted, mono- or di-substituted aryl groups phenyl or naphthyl, phenoxy, mono-, or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, or naphthyl group substituents are independently $C_1$-$C_6$ alkyl or $C_1$-$C_6$ alkoxy; or a mono-substituted phenyl, said phenyl having a substituent located at the para position, wherein the substituent is: a dicarboxylic acid residue, a diamine residue, an amino alcohol residue, a polyol residue, —$CH_2$—, —$(CH_2)_t$—, or —[O—$(CH_2)_t]_k$—, wherein t is from an integer 2, 3, 4, 5 or 6 and k is an integer from 1 to 50, the substituent being connected to an aryl group on another photochromic material; or $R^{19}$ and $R^{20}$ together form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings. Typically, $R^{19}$ and $R^{29}$ are each independently selected from $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, and substituted $C_2$-$C_6$ alkynyl. More specifically, $R^{19}$ and $R^{29}$ each independently can be selected from methyl, ethyl, propyl, butyl, pentyl and hexyl.

The substituents B and B' are each independently: an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently: hydroxyl, a group —C(=O)$R^{40}$, wherein $R^{40}$ is —$OR^{41}$, —$N(R^{42})R^{43}$, piperidino, or morpholino, wherein $R^{41}$ is allyl, $C_1$-$C_6$ alkyl, phenyl, mono($C_1$-$C_6$)alkyl substituted phenyl, mono($C_1$-$C_6$)alkoxy substituted phenyl, phenyl ($C_1$-$C_3$)alkyl, mono($C_1$-$C_6$)alkyl substituted phenyl($C_1$-$C_3$) alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, said halo substituent is chloro, fluoro, bromo or iodo, $R^{42}$ and $R^{43}$ are each independently $C_1$-$C_6$ alkyl, $C_6$-$C_7$ cycloalkyl, phenyl or substituted phenyl, the phenyl substituents being $C_1$-$C_6$ alkyl or $C_1$-$C_6$ alkoxy; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —[O—$(CH_2)_t]_k$—, wherein t is an integer 2, 3, 4, 5 or 6 and k is an integer from 1 to 50, the substituent being connected to an aryl group on another photochromic material; a group represented by one of:

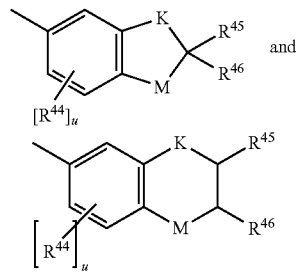

wherein K is —$CH_2$— or —O—, and M is —O— or substituted nitrogen, provided that when M is substituted nitrogen, K is —$CH_2$—, the substituted nitrogen substituents being hydrogen, $C_1$-$C_{12}$ alkyl, or $C_1$-$C_{12}$ acyl, each $R^{44}$ being independently chosen for each occurrence from $C_1$-$C_{12}$ alkyl, $C_1$-$C_{12}$ alkoxy, hydroxy, and halogen, $R^{45}$ and $R^{46}$ each being independently hydrogen or $C_1$-$C_{12}$ alkyl, and u is an integer ranging from 0 to 2; or a group represented by:

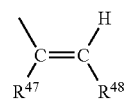

wherein $R^{47}$ is hydrogen or $C_1$-$C_{12}$ alkyl, and $R^{48}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen. Additionally, B and B' taken together can form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen.

In a particular embodiment, B and B' are each independently selected from phenyl and substituted phenyl. For example, B and B' each independently can be selected from a phenyl substituted with one or more groups independently selected from alkoxy, halogen, amino, perhaloalkoxy, acyl, carboxy, and alkoxycarbonyl. More specifically, B and B' each independently can be selected from a phenyl substituted with one group selected from, fluoro, chloro, and $CF_3$. Further, B and B' each independently can be 4-methoxyphenyl.

More specifically, the compound of Formula I of the present invention can include, but is not limited to, a compound chosen from:
3,3-bis-(4-methoxyphenyl)-7,12-bistrifluoromethyl-13,13-dimethyl-3H,13H-indeno[2,1-f]naphtho[1,2-b]pyran;
3,3-bis-(4-methoxyphenyl)-7,10-bistrifluoromethyl-13,13-dimethyl-3H,13H-indeno[2,1-f]naphtho[1,2-b]pyran;
3,3-diphenyl-7,12-bistrifluoromethyl-13,13-dimethyl-3H,13H-indeno[2,1-f]naphtho[1,2-b]pyran; and
3,3-diphenyl-7,10-bistrifluoromethyl-13,13-dimethyl-3H,13H-indeno[2,1-t]naphtho[1,2-b]pyran.

As used herein, in the specification and in the claims, the term "Hammett $\sigma_p$ value" refers to a measurement of the electronic influence, as either an electron-donating or electron-withdrawing influence, of a substituent attached to a carbon participating in an aromatic pi system that is transmitted through the polarizable pi electron system, such as, for example, an aromatic pi electron system. The Hammett $\sigma_p$ value is a relative measurement comparing the electronic influence of the substituent in the para position of a phenyl ring to the electronic influence of a hydrogen substituted at the para position. Typically for aromatic substituents in general, a negative Hammett $\sigma_p$ value is indicative of a group or substituent having an electron-donating influence on a pi electron system (i.e., an electron-donating group) and a positive Hammett $\sigma_p$ value is indicative of a group or substituent having an electron-withdrawing influence on a pi electron system (i.e., an electron-withdrawing group).

As used herein, the term "electron-donating group" may be defined as a group that donates electron density into a pi-system, such as, for example, of the indeno-fused naphthopyran core structure. Examples of an "electron-donating group" may include an atom bonded directly to the pi-system of the photochromic material, wherein the atom has at least one lone pair of electrons which are capable of delocalization into the pi system of the aromatic ring structure, and/or the group may donate electron density into the pi system by an inductive effect, such as, for example, an alkyl substituent. Further, an "electron-donating group", as used herein, may be defined as a group having a negative Hammett $\sigma_p$ value, when the group is attached to a carbon participating in an aromatic pi system.

Electron-withdrawing groups suitable for use in connection with various non-limiting embodiments of the compound of Formula I described herein may have a Hammett $\sigma_p$ value ranging from about 0.05 to about 0.85, such as from 0.05 to 0.75. Suitable electron-withdrawing groups may comprise, for example and without limitation: nitro ($\sigma_p$=0.81), halogen, such as fluoro ($\sigma_p$=0.06), chloro ($\sigma_p$=0.23), and bromo ($\sigma_p$=0.23); perfluoroalkyl (for example, —$CF_3$, $\sigma_p$=0.54) or perfluoroalkoxy (for example, —$OCF_3$, $\sigma_p$=0.35), where the perfluoroalkyl portion of either the perfluoroalkyl or the perfluoroalkoxy may comprise, for example, trifluoromethyl or other perfluoroalkyl portions having the formula $C_nF_{2n+1}$, where 'n' is an integer from 1 to 10; cyano ($\sigma_p$=0.66); —OC(=O)$R^0$ (for example, —OC(=O)$CH_3$, $\sigma_p$=0.31); —$SO_2X$ (for example, —$SO_2CH_3$, $\sigma_p$=0.68); or —C(=O)—X, where X is hydrogen (—CHO, $\sigma_p$=0.22), $C_1$-$C_6$ alkyl (for example, —C(=O)$CH_3$, $\sigma_p$=0.50), —$OR^1$ ($\sigma_p$≈0.4), or —$NR^2R^3$ (for example, —C(=O)$NH_2$, $\sigma_p$=0.36), wherein each of $R^0$, $R^1$, $R^2$, and $R^3$ may each independently be hydrogen, $C_1$-$C_6$ alkyl, $C_5$-$C_1$ cycloalkyl, phenyl, mono-substituted phenyl, di-substituted phenyl, alkylene glycol, or polyalkylene glycol, wherein the phenyl substituents may be $C_1$-$C_6$ alkyl or $C_1$-$C_6$ alkoxy. Further suitable electron-withdrawing substituents having Hammett $\sigma_p$ values in the range from about 0.05 to about 0.85 are set forth in "Section 9 Physicochemical Relationships" in *Lange's Handbook of Chemistry*, 15$^{th}$ ed. J. A. Dean, editor, McGraw Hill, 1999, pp 9.1-9.8, the disclosure of which is incorporated herein by reference. It will be appreciated by those skilled in the art that the subscript "p", when used in connection with the Hammett σ value, refers to the Hammett $\sigma_p$ value as measured when the group is located at the para position of a phenyl ring of a model system, such as a para-substituted benzoic acid model system.

As previously mentioned, the compound of the present invention represented by Formula I described in detail above can comprise a photochromic material. Such photochromic material may be used in those applications in which photochromic materials may be employed, such as, optical elements, for example, an ophthalmic element, a display element, a window, a mirror, an active liquid crystal cell element, or a passive liquid crystal cell element. As used herein, the term "optical" means pertaining to or associated with light and/or vision. As used herein, the term "ophthalmic" means pertaining to or associated with the eye and vision. As used herein, the term "display" means the visible or machine-readable representation of information in words, numbers, symbols, designs or drawings. Non-limiting examples of display elements include screens, monitors, and security elements, such as security marks. As used herein, the term "window" means an aperture adapted to permit the transmission of radiation therethrough. Non-limiting examples of windows include aircraft and automotive windshields, automotive and aircraft transparencies, e.g., T-roofs, sidelights and backlights, filters, shutters, and optical switches. As used herein, the term "mirror" means a surface that specularly reflects a large fraction of incident light. As used herein, the term "liquid crystal cell" refers to a structure containing a liquid crystal material that is capable of being ordered. One non-limiting example of a liquid crystal cell element is a liquid crystal display.

The photochromic materials comprising the compound of Formula I of the present invention may be used in an ophthalmic element, such as, corrective lens(es), including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument, such as a camera or telescope lens. In other non-limiting embodiments, the photochromic materials of the present disclosure may be used in plastic films and sheets, textiles, and coatings.

Further, it is contemplated that the photochromic materials disclosed herein may each be used alone, in combination with other photochromic materials, or in combination with an appropriate complementary conventional photochromic material (i.e., in photochromic compositions). For example, the photochromic materials may be used in conjunction with conventional photochromic materials having activated absorption maxima within the range of about 400 to about 800 nanometers. Further, the photochromic materials may be used in conjunction with a complementary conventional polymerizable or a compatiblized photochromic material, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

As discussed above, the photochromic compositions may contain a mixture of photochromic materials. For example, although not limiting herein, mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Thus, the present invention provides a photochromic composition comprising an organic material, said organic material being at least one of polymeric material, an oligomeric material and a monomeric material, and a photochromic material according to any of the non-limiting embodiments of set forth above incorporated into at least a portion of the organic material. The photochromic material may be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof.

As discussed above, the photochromic compositions disclosed herein may comprise an organic material chosen from a polymeric material, an oligomeric material and/or a monomeric material. Examples of polymeric materials that may be used can include, without limitation: polymers of bis(allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene)dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(α-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, where transparency of the photochromic composition is desired, the organic material may be a transparent polymeric material. For example, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other co-polymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and co-polymers of styrene with methyl methacrylate, vinyl acetate and acrylonitrile. The polymeric material can include optical resins sold by PPG Industries, Inc. under the CR®-designation, such as, for example, CR-307, CR-407, and CR-607.

Further, the organic material may be a polymeric material chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

In addition to the foregoing, the present invention provides a photochromic article comprising a substrate (such as any of the optical substrate materials described above, and a photochromic material according to any of the non-limiting embodiments discussed above connected to or incorporated into a portion of the substrate. As used herein, the term "connected to" means associated with, either directly or indirectly through another material or structure. The photochromic article of the present invention may be an optical element, for example, but not limited to, an ophthalmic element, a display element, a window, a mirror, an active liquid crystal cell element, and a passive liquid crystal cell element. The photochromic article can be an ophthalmic element, for example, but not limited to, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument.

Where the substrate of the photochromic article comprises a polymeric material, the photochromic material may be connected to at least a portion of the substrate by incorporating the photochromic material into at least a portion of the polymeric material of the substrate, or at least a portion of the oligomeric or monomeric material from which the substrate is formed. For example, the photochromic material may be incorporated into the polymeric material of the substrate by the cast-in-place method. Additionally or alternatively, the photochromic material may be incorporated into at least a portion of the polymeric material of the substrate by substituted. Imbibition and the cast-in-place method are discussed below.

Also, the photochromic material may be connected to at least a portion of the substrate of the photochromic article as part of an at least partial coating that is connected to at least a portion of a substrate. In such an instance, the substrate may be a polymeric substrate or an inorganic substrate (such as, but not limited to, a glass substrate). Further, the photochromic material (which includes the compound of Formula I of the present invention) may be incorporated into at least a portion of the coating composition prior to application of the coating composition to the substrate, or alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

For example, the photochromic article may comprise an at least partial coating of a polymeric material connected to at least a portion of a surface thereof. According to this non-limiting embodiment, the photochromic material may be blended and/or bonded with at least a portion of the polymeric material of the at least partial coating.

The at least partial coating comprising a photochromic material may be directly connected the substrate, for example, by directly applying a coating composition comprising a photochromic material to at least a portion of a surface of the substrate, and at least partially setting the coating composition. Additionally or alternatively, the at least partial coating comprising a photochromic material may be connected to the substrate, for example, through one or more additional coatings. For example, while not limiting herein, an additional coating composition may be applied to at least a portion of the surface of the substrate, at least partially set, and thereafter the coating composition comprising a photochromic material may be applied over the additional coating and at least partially set. Non-limiting methods of applying coatings compositions to substrates are discussed herein below.

Non-limiting examples of additional coatings and films that may be used in conjunction with the photochromic articles disclosed herein include primer or compatiblizing coatings; protective coatings, including transitional coatings, abrasion-resistant coatings and other coating that protect against the effects of polymerization reaction chemicals and/or protect against deterioration due to environmental conditions such as moisture, heat, ultraviolet light, oxygen (e.g., UV-shielding coatings and oxygen barrier-coatings); antireflective coatings; conventional photochromic coating; and polarizing coatings and polarizing stretched-films; and combinations thereof.

Non-limiting examples of primer or compatiblizing coatings that may be used in conjunction with various non-limiting embodiments disclosed herein include coatings comprising coupling agents, at least partial hydrolysates of coupling agents, and mixtures thereof. As used herein "coupling agent" means a material having a group capable of reacting, binding and/or associating with a group on a surface. Coupling agents according to various non-limiting embodiments disclosed herein may include organometallics such as silanes, titanates, zirconates, aluminates, zirconium aluminates, hydrolysates thereof and mixtures thereof. As used herein the phrase "at least partial hydrolysates of coupling agents" means that some to all of the substituted groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating" means a coating that aids in creating a gradient in properties between two coatings. For example, although not limiting herein, a transitional coating may aid in creating a gradient in hardness between a relatively hard coating (such as an abrasion-resistant coating) and a relatively soft coating (such as a photochromic coating). Non-limiting examples of transitional coatings include radiation-cured, acrylate-based thin films as described in U.S. Patent Application Publication 2003/0165686 at paragraphs [0079]-[0173], which are hereby specifically incorporated by reference herein.

As used herein the term "abrasion-resistant coating" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion-resistant coatings include abrasion-resistant coatings comprising organosilanes, organosiloxanes, abrasion-resistant coatings based on inorganic materials such as silica, titania and/or zirconia, and organic abrasion-resistant coatings of the type that are ultraviolet light curable.

Non-limiting examples of antireflective coatings include a monolayer, multilayer coatings of metal oxides, metal fluorides, or other such materials, which may be deposited onto the articles disclosed herein (or onto self supporting films that are applied to the articles), for example, through vacuum deposition, sputtering, etc.

Non-limiting examples of conventional photochromic coatings include, but are not limited to, coatings comprising conventional photochromic materials.

Non-limiting examples of polarizing coatings and polarizing stretched-films include, but are not limited to, coatings (such as those described in U.S. Patent Application Publication No. 2005/0151926), and stretched-films comprising dichroic compounds that are known in the art.

As discussed herein, an additional at least partial coating or film may be formed on the substrate prior to forming the coating comprising the photochromic material on the substrate. For example, a primer or compatilibizing coating may be formed on the substrate prior to applying the coating composition comprising the photochromic material. Additionally or alternatively, an additional at least partial coating may be formed on the substrate after forming coating comprising the photochromic material on the substrate, for example, as an overcoating on the photochromic coating. For example a transitional coating may be formed over the coating comprising the photochromic material, and an abrasion-resistant coating may be formed over the transitional coating.

For example, there is provided a photochromic article comprising a substrate (such as, but not limited to a plano-concave or a plano-convex ophthalmic lens substrate), which comprises an abrasion-resistant coating on at least a portion of a surface thereof; a primer or compatiblizing coating on at least a portion of the abrasion-resistant coating; a photochromic coating comprising a photochromic material according to various non-limiting embodiments disclosed herein on at least a portion of the primer or compatiblizing coating; a transitional coating on at least a portion of the photochromic coating; and an abrasion-resistant coating on at least a portion of the transitional coating. Further, the photochromic article may also comprise, for example, an antireflective coating that is connected to a surface of the substrate and/or a polarizing coating or film that is connected to a surface of the substrate.

Non-limiting methods of making photochromic compositions and photochromic articles, such as optical elements, will now be discussed. One non-limiting embodiment provides a method of making a photochromic composition, the method comprising incorporating a photochromic material into at least a portion of an organic material. Non-limiting methods of incorporating photochromic materials into an organic material include, for example, mixing the photochromic material into a solution or melt of a polymeric, oligomeric, or monomeric material, and subsequently at least partially setting the polymeric, oligomeric, or monomeric material (with or without bonding the photochromic material to the organic material); and imbibing the photochromic material into the organic material (with or without bonding the photochromic material to the organic material).

Another non-limiting embodiment provides a method of making a photochromic article comprising connecting a photochromic material according to various non-limiting embodiments discussed above, to at least a portion of a substrate. For example, if the substrate comprises a polymeric material, the photochromic material may be connected to at least a portion of the substrate by at least one of the cast-in-place method and/or by imbibition. For example, in the cast-in-place method, the photochromic material may be mixed with a polymeric solution or melt, or other oligomeric and/or monomeric solution or mixture, which are subsequently cast into a mold having a desired shape and at least partially set to form the substrate. Optionally, the photochromic material may be bonded to a portion of the polymeric material of the substrate, for example, by co-polymerization with a monomeric precursor thereof. In the imbibition method, the photochromic material may be diffused into the polymeric material of the substrate after it is formed, for example, by immersing a substrate in a solution containing the photochromic material, with or without heating. Thereafter, although not required, the photochromic material may be bonded with the polymeric material.

Other non-limiting embodiments disclosed herein provide a method of making an optical element comprising connecting a photochromic material to at least a portion of a substrate by at least one of in-mold casting, coating and lamination. For example, according to one non-limiting embodiment, wherein the substrate comprises a polymeric material, the photochromic material may be connected to at least a portion of a substrate by in-mold casting. According to this non-limiting embodiment, a coating composition comprising the photochromic material, which may be a liquid coating composition or a powder coating composition, is applied to the surface of a mold and at least partially set. Thereafter, a polymer solution or melt, or oligomeric or monomeric solution or mixture is cast over the coating and at least partially set. After setting, the coated substrate is removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

Further, where the substrate comprises a polymeric material or an inorganic material such as glass, the photochromic material may be connected to at least a portion of a substrate by coating. Non-limiting examples of suitable coating methods include spin coating, spray coating (e.g., using a liquid or powder coating), curtain coating, roll coating, spin and spray coating, over-molding, and combinations thereof. For example, the photochromic material may be connected to the substrate by over-molding. According to this non-limiting embodiment, a coating composition comprising the photochromic material (which may be a liquid coating composition or a powder coating composition as previously discussed) may be applied to a mold and then the substrate may be placed into the mold such that the substrate contacts the coating causing it to spread over at least a portion of the surface of the substrate. Thereafter, the coating composition may be at least partially set and the coated substrate may be removed from the mold. Alternatively, over-molding may be done by placing the substrate into a mold such that an open region is defined between the substrate and the mold, and thereafter injecting a coating composition comprising the photochromic material into the open region. Thereafter, the coating composition may be at least partially set and the coated substrate may be removed from the mold.

Additionally or alternatively, a coating composition (with or without a photochromic material) may be applied to a substrate (for example, by any of the foregoing methods), the coating composition may be at least partially set, and thereafter, a photochromic material may be imbibed (as previously discussed) into the coating composition.

Additionally, where the substrate comprises a polymeric material or an inorganic material such as glass, the photochromic material may be connected to at least a portion of a substrate by lamination. According to this non-limiting embodiment, a film comprising the photochromic material may be adhered or otherwise connect to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, the present invention contemplates the use of various combinations of the forgoing methods to form photochromic articles. For example, and without limitation herein, a photochromic material may be connected to substrate by incorporation into an organic material from which the substrate is formed (for example, using the cast-in-place method and/or imbibition), and thereafter a photochromic material (which may be the same or different from the aforementioned photochromic material) may be connected to a portion of the substrate using the in-mold casting, coating and/or lamination methods discussed above.

Further, it will be appreciated by those skilled in the art that the photochromic compositions and articles disclosed herein may further comprise other additives that aid in the processing and/or performance of the composition or article. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

According to various non-limiting embodiments, the photochromic materials described herein may be used in amounts (or ratios) such that the organic material or substrate into which the photochromic materials are incorporated or otherwise connected exhibits desired optical properties. For example, the amount and types of photochromic materials may be selected such that the organic material or substrate may be clear or colorless when the photochromic material is in the closed-form (i.e., in the bleached or unactivated state) and may exhibit a desired resultant color when the photochromic material is in the open-form (that is, when activated by actinic radiation). The precise amount of the photochromic material to be utilized in the various photochromic compositions and articles described herein, is not critical provided that a sufficient amount is used to produce the desired effect. It should be appreciated that the particular amount of the photochromic material used may depend on a variety of factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that is incorporated into an organic material may range from 0.01 to 40 weight percent based on the weight of the organic material.

Various non-limiting embodiments disclosed herein will now be illustrated in the following non-limiting examples.

EXAMPLES

Part 1 describes the preparation of Examples 1-4 and Comparative Examples (CE) 1-2. Part 2 describes the testing of the photochromic properties of the Examples and Comparative Examples.

Part 1

Preparation of Examples 1-4 and Comparative Examples 1-2

Example 1

Step 1

Potassium t-butoxide (26.4 grams) was weighed into a 2 liter reaction flask equipped with a mechanical stirrer, placed under a nitrogen atmosphere and 1200 milliliters (mL) of toluene was added followed by 3,3'-bistrifluoromethylbenzophenone (50 grams). The reaction mixture was stirred mechanically and heated to 50° C. Dimethyl succinate (28.7 grams) was added to the reaction mixture over a 30 minute period. The reaction mixture became viscous and 100 mL of toluene was added to dilute the reaction mixture. The reaction mixture was heated at 70° C. for 4 hours. After cooling to room temperature, the reaction mixture was poured into 1000 mL of water and the toluene layer discarded. The aqueous layer was extracted with diethyl ether (2×700 mL) to remove the neutral products, and then acidified the aqueous layer with concentrated hydrochloric acid. A yellow oily liquid was obtained from the aqueous layer, and was extracted with 2×600 mL of methylene chloride. The organic layers were combined, washed with saturated NaCl solution (1×700 mL) and dried over anhydrous sodium sulfate. Removal of the solvent by rotary evaporation yielded 65 grams of a mixture of (E and Z) 4,4-(bis(3-trifluoromethylphenyl))-3-methoxycarbonyl-3-butenoic acids as a brownish yellow oil. This material was not purified further and was used directly in the next step.

Step 2

The product of Step 1 (mixture of E and Z isomers of 4,4-(bis(3-trifluoromethylphenyl))-3-methoxycarbonyl-3-butenoic acids, 65 grams) and acetic anhydride (250 mL) were added to a reaction flask. The reaction mixture was heated to reflux for 6 hours under a nitrogen atmosphere. The reaction mixture was cooled to room temperature and subsequently the excess acetic anhydride was removed by rotary evaporation to yield 68.6 grams of 1-(3-trifluoromethylphenyl)-2-methoxycarbonyl-4-acetoxy-7-trifluoromethyl naphthalene. The product was used without further purification in the subsequent reaction.

Step 3

The product of Step 2 (1-(3-trifluoromethylphenyl)-2-methoxycarbonyl-4-acetoxy-7-trifluoromethyl naphthalene, 68.6 grams) and 400 mL of methanol were combined in a reaction flask. Added 12 mL of concentrated hydrochloric acid to the reaction flask, and heated to reflux overnight under a nitrogen atmosphere. The reaction mixture was cooled to room temperature and then at 0° C. White crystals of the desired product (1-(3-trifluoromethylphenyl)-2-methoxycarbonyl-4-hydroxy-7-trifluoromethyl naphthalene) were obtained, and subsequently filtered off and dried under vacuum to get 31.17 grams of product. This material was not purified further but was used directly in the next step.

Step 4

The product of Step 3 (1-(3-trifluoromethylphenyl)-2-methoxycarbonyl-4-hydroxy-7-trifluoromethyl naphthalene, 31 grams) was added to a reaction flask containing 250 mL of tetrahydrofuran. The resulting mixture was stirred at room temperature under a nitrogen atmosphere. Methyl magnesium chloride solution (98.8 mL of a 3M in tetrahydrofuran) was added dropwise over thirty minutes. The resulting yellow reaction mixture was heated to reflux temperatures for 4 hours. The reaction mixture was cooled to room temperature, poured into 500 mL of saturated NaCl solution, and then neutralized with concentrated hydrochloric acid till acidic. The mixture was extracted with two 300 mL portions of ether, and the organic portions were combined and washed with 700 mL of saturated NaCl solution. The organic layer was dried over anhydrous sodium sulfate and concentrated by rotary evaporation. The resulting brown oil (31 grams) was transferred into a reaction vessel (fitted with a Dean-Stark trap) containing 200 mL of xylene to which 1.5 grams of para-toluene sulfonic acid was added. The reaction mixture was heated to reflux for 4 hours and cooled. The xylene was removed via rotary evaporation to obtain a brownish oil. TLC analysis indicated 2 products. The brownish oil was purified via flash column chromatography on a silica gel column using a mixture of hexane, methylene chloride and ethyl acetate (70/25/5) as the eluant. The top (less polar) spot was 2,8-bistrifluoromethyl-7,7-dimethyl-5-hydroxy-7H-benzo[C]

fluorene (obtained 14.4 grams after combining the fractions) while the second (more polar) spot was 2,10-bistrifluoromethyl-7,7-dimethyl-5-hydroxy-7H-benzo[C]fluorene (obtained 6.6 grams after combining the fractions).

Step 5

The less polar product of Step 4 (2,8-bistrifluoromethyl-7,7-dimethyl-5-hydroxy-7H-benzo[C]fluorene, 2.73 grams), 1,1-bis-(4-methoxyphenyl)-2-propyn-1-ol (2.34 grams), 12 drops of methane sulfonic acid and 250 mL of methylene chloride were combined in a reaction flask and stirred overnight under a nitrogen atmosphere. The reaction mixture was washed carefully with a mixture of 250 mL of a saturated sodium bicarbonate solution and 250 mL of water. The organic layer was separated, dried over sodium sulfate, and concentrated by rotary evaporation to get a brown solid. This brown solid was purified via flash column chromatography on a silica gel column using a mixture of hexane and methylene chloride (70/30) as the eluant to yield 2.0 grams of an off white solid. A NMR spectrum showed the product to have a structure consistent with 3,3-bis-(4-methoxyphenyl)-7,12-bistrifluoromethyl-13,13-dimethyl-3H,13H-indeno[2,1-f]naphtho[1,2-b]pyran as represented by the following graphic formula.

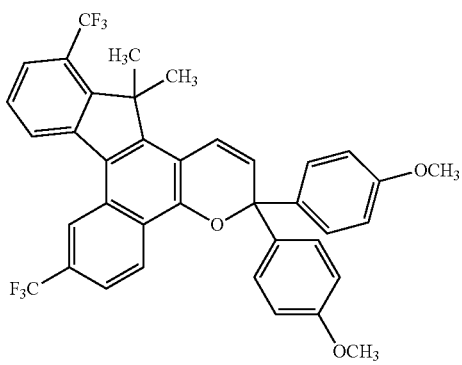 [SMILES: COc1ccc(C2(c3ccc(OC)cc3)C=Cc3c4c(c5cc(C(F)(F)F)ccc5c3O2)-c2cccc(C(F)(F)F)c2C4(C)C)cc1]

Example 2

Step 1

The more polar product of Example 1, Step 4 (2,10-bistrifluoromethyl-7,7-dimethyl-5-hydroxy-7H-benzo[C]fluorene, 2.6 grams), 1,1-bis-(4-methoxyphenyl)-2-propyn-1-ol (2.26 grams), 14 drops of methane sulfonic acid and 250 mL of methylene chloride were combined in a reaction flask and stirred overnight under a nitrogen atmosphere. The reaction mixture was washed carefully with a mixture of 250 mL of a saturated sodium bicarbonate solution and 250 mL of water. The organic layer was separated, dried over sodium sulfate, and concentrated by rotary evaporation to get a brown solid. This brown solid was purified via flash column chromatography on a silica gel column using a mixture of hexane and ethyl acetate (80/20) as the eluant to yield 1.5 grams of an off white solid. A NMR spectrum showed the product to have a structure consistent with 3,3-bis-(4-methoxyphenyl)-7,10-bistrifluoromethyl-13,13-dimethyl-3H,13H-indeno[2,1-f]naphtho[1,2-b]pyran as represented by the following graphic formula.

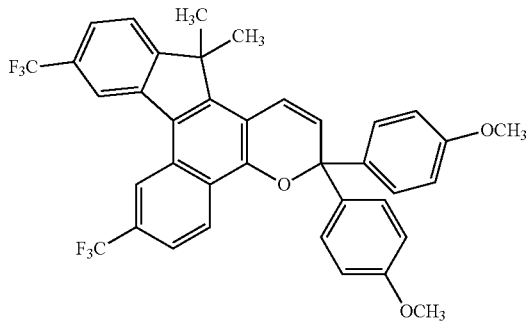 [SMILES: COc1ccc(C2(c3ccc(OC)cc3)C=Cc3c4c(c5cc(C(F)(F)F)ccc5c3O2)-c2cc(C(F)(F)F)ccc2C4(C)C)cc1]

Example 3

Step 1

The less polar product of Example 1, Step 4 (2,8-bistrifluoromethyl-7,7-dimethyl-5-hydroxy-7H-benzo[C]fluorene, 4.07 grams), 1,1-diphenyl-2-propyn-1-ol (2.14 grams), 10 drops of trifluoroacetic acid, 5 drops of methane sulfonic acid and 200 mL of methylene chloride were combined in a reaction flask and stirred for 4 hours under a nitrogen atmosphere. The reaction mixture was washed carefully with a mixture of 100 mL of a saturated sodium bicarbonate solution and 100 mL of water. The organic layer was separated, dried over sodium sulfate, and concentrated by rotary evaporation to get a brown solid. This brown solid was purified by crystallization from diethyl ether to yield 4.3 grams of a white solid. A NMR spectrum showed the product to have a structure consistent with 3,3-diphenyl-7,12-bistrifluoromethyl-13,13-dimethyl-3H,13H-indeno[2,1-f]naphtho[1,2-b]pyran as represented by the following graphic formula.

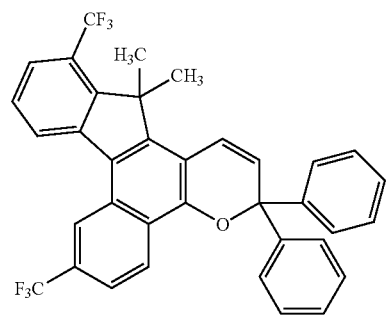 [SMILES: CC1(C)c2c(cccc2C(F)(F)F)-c2c1c1c(c3ccc(C(F)(F)F)cc23)OC(c2ccccc2)(c2ccccc2)C=C1]

Example 4

Step 1

The more polar product of Example 1, Step 4 (2,10-bistrifluoromethyl-7,7-dimethyl-5-hydroxy-7H-benzo[C]fluorene, 1.95 grams), 1,1-diphenyl-2-propyn-1-ol (1.02 grams), 10 drops of trifluoroacetic acid, 4 drops of methane sulfonic acid and 1250 mL of methylene chloride were combined in a reaction flask and stirred for 2 hours under a nitrogen atmosphere. The reaction mixture was washed carefully with a mixture of 100 mL of a saturated sodium bicarbonate solution and 100 mL of water. The organic layer was separated, dried over sodium sulfate, and concentrated by rotary evaporation to get a brown solid. This brown solid was purified by crystallization from a 1:1 mixture of diethyl ether and hexane to yield 2.1 grams of a white solid. A NMR spectrum showed the product to have a structure consistent with 3,3-diphenyl-7,10-bistrifluoromethyl-13,13-dimethyl-3H,13H-indeno[2,1-f]naphtho[1,2-b]pyran as represented by the following graphic formula.

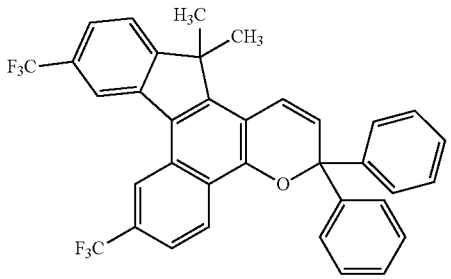 [SMILES: CC1(C)c2ccc(C(F)(F)F)cc2-c2c1c1c(c3ccc(C(F)(F)F)cc23)OC(c2ccccc2)(c2ccccc2)C=C1]

Comparative Example 1

CE-1

CE-1 was prepared following the disclosure of U.S. Pat. No. 5,645,767, which disclosure is incorporated herein by reference, and is reported to be 3,3-bis-(4-methoxyphenyl)-13,13-dimethyl-3H,13H-indeno[2,1-f]naphtho[1,2-b]pyran as represented by the following graphic formula.

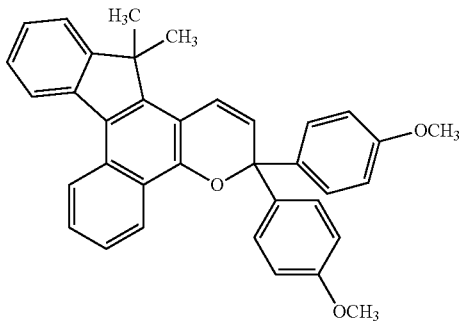 [SMILES: COc1ccc(C2(c3ccc(OC)cc3)C=Cc3c4c(c5ccccc5c3O2)-c2ccccc2C4(C)C)cc1]

Comparative Example 2

CE-2

CE-2 was prepared following the disclosure of U.S. Pat. No. 5,645,767, which disclosure is incorporated herein by reference, and is reported to be 3,3-diphenyl-13,13-dimethyl-3H,13H-indeno[2,1-f]naphtho[1,2-b]pyran as represented by the following graphic formula.

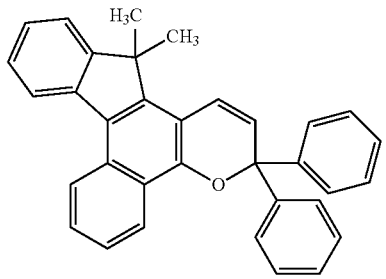 [SMILES: CC1(C)c2ccccc2-c2c1c1c(c3ccccc23)OC(c2ccccc2)(c2ccccc2)C=C1]

Part 2

Photochromic Property Testing

Part 2A—Test Square Preparation

Testing was done with the compounds described in Examples 1-4, and CE 1-2 in the following manner. A quantity of compound calculated to yield a 1.5×10-3 molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on the optical bench, the photochromic test squares from Part 2A were exposed to 365 nm ultraviolet light for about 30 minutes at a distance of about 14 cm from the source to cause the photochromic material to transform from the ground state-form to an activated-state form, and then placed in a 75° C. oven for about 20 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.). The bench was fitted with a 300-watt xenon arc lamp, a remote controlled shutter, a Melles Griot KG2 filter that modifies the UV and IR wavelengths and acts as a heat-sink, neutral density filter(s) and a sample holder, situated within a water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The λmax-vis is the wavelength in the visible spectrum at which the maximum absorption of the activated-state form of the photochromic compound in a test square occurs. The λmax-vis wavelength was determined by testing the photochromic test squares in a Varian Cary 300 UV-Visible spectrophotometer; it can also be calculated from the spectrum obtained by the S2000 spectrometer on the optical bench.

The results are listed in Table I. Comparative Example 1 is similar in structure and should be compared to Examples and 2. Comparative Example 2 is similar in structure and should be compared to Examples 3 and 4.

TABLE 1

Photochromic Performance Test Results

| Example # | $\lambda_{max\text{-}vis}$ (nm) | ΔOD at saturation | T ½ (sec) |
|---|---|---|---|
| 1 | 562 | 0.11 | 11 |
| 2 | 565 | 0.15 | 16 |
| 3 | 531 | 0.55 | 53 |
| 4 | 536 | 0.72 | 80 |
| CE 1 | 561 | 0.78 | 129 |
| CE 2 | 532 | 1.50 | 723 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

I claim:

1. A compound of Formula I

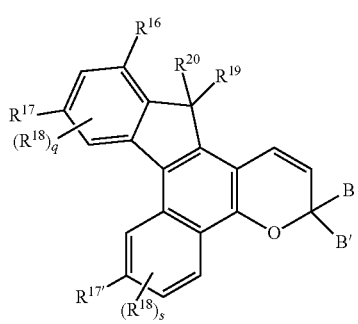

Formula I wherein, $R^{16}$ and $R^{17'}$ are each independently selected from an electron withdrawing group having a Hammett $\sigma_p$ value of from 0.05 to 0.85, and $R^{17}$ is hydrogen;

$R^{18}$ is independently for each occurrence: hydrogen; halogen; $C_1$-$C_6$ alkyl; $C_1$-$C_4$ haloalkyl; $C_3$-$C_7$ cycloalkyl; substituted or unsubstituted phenyl; —$OR^{29}$ or —OC(=O)$R^{29}$, wherein $R^{29}$ is hydrogen, $C_1$-$C_6$ alkyl, phenyl ($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and said phenyl substituents are $C_1$-$C_6$ alkyl or $C_1$-$C_6$ alkoxy; a mono-substituted phenyl, said phenyl having a substituent located at the para position, wherein the substituent is: a dicarboxylic acid residue, a diamine residue, an amino alcohol residue, a polyol residue, —$CH_2$—, —$(CH_2)_t$—, or —[O—$(CH_2)_t]_k$—, wherein t is the integer 2, 3, 4, 5 or 6 and k is an integer from 1 to 50, the substituent being connected to an aryl group on another photochromic material; —$N(R^{30})R^{31}$, wherein $R^{30}$ and $R^{31}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or ($C_1$-$C_6$)alkoxy($C_1$-$C_6$)alkyl, wherein said aryl group is phenyl or naphthyl, or $R^{30}$ and $R^{31}$ come together with the nitrogen atom to form a $C_3$-$C_{20}$ hetero-bicycloalkyl ring or a $C_4$-$C_{20}$ hetero-tricycloalkyl ring; a nitrogen containing ring represented by the following graphic formula IVA:

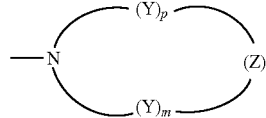

IVA wherein each —Y— is independently chosen for each occurrence from —$CH_2$—, —$CH(R^{32})$—, —$C(R^{32})_2$—, —CH(aryl)-, —C(aryl)$_2$-, and —$C(R^{32})$(aryl)-, and Z is —Y—, —O—, —S—, —S(O)—, —$SO_2$—, —NH—, —$N(R^{32})$—, or —N(aryl)-, wherein each $R^{32}$ is independently $C_1$-$C_6$ alkyl or hydroxy($C_1$-$C_6$)alkyl, each aryl is independently phenyl or naphthyl, m is an integer 1, 2 or 3, and p is an integer 0, 1, 2, or 3 and when p is 0, Z is —Y—; a group represented by one of the following graphic formulae IVB or IVC:

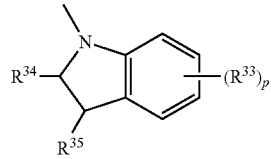

IVB

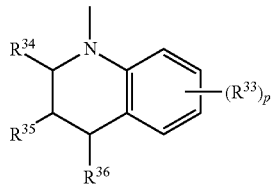

IVC wherein $R^{34}$, $R^{35}$, and $R^{36}$ are each independently hydrogen, $C_1$-$C_6$ alkyl, phenyl, or naphthyl, or the groups $R^{34}$ and $R^{35}$ together form a ring of 5 to 8 carbon atoms and each $R^{33}$ is independently for each occurrence from $C_1$-$C_6$ alkyl, $C_1$-$C_6$ alkoxy, or halogen and p is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_6$)alkyl;

q is an integer from 0 to 2;

s is an integer from 0 to 3;

$R^{19}$ and $R^{20}$ are each independently: hydrogen; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W is hydrogen, hydroxy, $C_1$-$C_6$ alkyl, $C_1$-$C_6$ alkoxy, the unsubstituted, mono- or di-substituted aryl groups phenyl or naphthyl, phenoxy, mono- or di-($C_1$-$C_6$)alkoxy substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; —OR$^{37}$, wherein R$^{37}$ is $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group —CH(R$^{38}$)Y'', wherein R$^{38}$ is hydrogen or $C_1$-$C_3$ alkyl and Y'' is CN, CF$_3$, or COOR$^{39}$, wherein R$^{39}$ is hydrogen or $C_1$-$C_3$ alkyl, or R$^{37}$ is the group, —C(=O)W', wherein W' is hydrogen, $C_1$-$C_6$ alkyl, $C_1$-$C_6$ alkoxy, the unsubstituted, mono- or di-substituted aryl groups phenyl or naphthyl, phenoxy, mono-, or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, or naphthyl group substituents are independently $C_1$-$C_6$ alkyl or $C_1$-$C_6$ alkoxy; or a mono-substituted phenyl, said phenyl having a substituent located at the para position, wherein the substituent is: a dicarboxylic acid residue, a diamine residue, an amino alcohol residue, a polyol residue, —CH$_2$—, —(CH$_2$)$_t$—, or —[O—(CH$_2$)$_t$]$_k$—, wherein t is from an integer 2, 3, 4, 5 or 6 and k is an integer from 1 to 50, the substituent being connected to an aryl group on another photochromic material; or R$^{19}$ and R$^{20}$ together form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings; and B and B' are each independently: an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl; benzopyridyl, indolinyl, and fluorenyl, wherein each of the phenyl, aryl and heteroaromatic substituents are each independently: hydroxyl, a group —C(=O)R$^{40}$, wherein R$^{40}$ is —OR$^{41}$, —N(R$^{42}$)R$^{43}$, piperidino, or morpholino, wherein R$^{41}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, said halo substituent is chloro, fluoro, bromo or iodo, R$^{42}$ and R$^{43}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, wherein t is an integer 2, 3, 4, 5 or 6 and k is an integer from 1 to 50, the substituent being connected to an aryl group on another photochromic material; a group represented by one of:

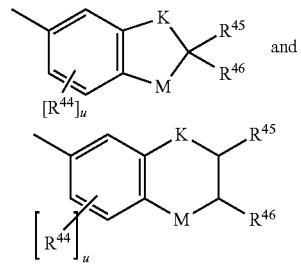

wherein K is —CH$_2$— or —O—, and M is —O— or substituted nitrogen, provided that when M is substituted nitrogen, K is —CH$_2$—, the substituted nitrogen substituents being hydrogen, $C_1$-$C_{12}$ alkyl, or $C_1$-$C_{12}$ acyl, each R$^{44}$ being independently chosen for each occurrence from $C_1$-$C_{12}$, alkyl, $C_1$-$C_{12}$ alkoxy, hydroxy, and halogen, R$^{45}$ and R$^{46}$ each being independently hydrogen or $C_1$-$C_{12}$ alkyl, and u is an integer ranging from 0 to 2; or a group represented by:

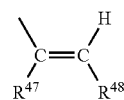

wherein R$^{47}$ is hydrogen or $C_1$-$C_{12}$ alkyl, and R$^{48}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen; or B and B' taken together form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen.

2. The compound of claim 1, wherein R$^{16}$ and R$^{17'}$ are each independently selected from fluoro, chloro, bromo, haloalkyl, haloalkoxy, cyano, nitro, sulfonyl, sulfonate, —OC(=O)R$^0$, or —C(=O)—X, wherein X is hydrogen, $C_1$-$C_6$ alkyl, —OR$^1$ or —NR$^2$R$^3$, wherein R$^0$, R$^1$, R$^2$ and R$^3$ are each independently hydrogen, $C_1$-$C_6$ alkyl, $C_5$-$C_7$ cycloalkyl, phenyl, mono-substituted phenyl, disubstituted phenyl, alkylene glycol, or polyalkylene glycol, wherein said mono- and disubstituted phenyl substituents are $C_1$-$C_6$ alkyl or $C_1$-$C_6$ alkoxy.

3. The compound of claim 2 wherein R$^{16}$ and R$^{17'}$ are each independently selected from $C_1$-$C_4$ haloalkyl, chloro, fluoro, cyano, nitro, —OC(=O)R$^0$ or —C(=O)—X, wherein X is —OR$^1$ wherein R$^0$ and R$^1$ are each independently $C_1$-$C_4$ alkyl.

4. The compound of claim 3 wherein R$^{16}$ and R$^{17'}$ are each independently selected from CF$_3$, CF$_2$CF$_3$, chloro, fluoro, cyano, nitro, acetyl, propionyl, methoxycarbonyl, and ethoxycarbonyl.

5. The compound of claim 1, wherein R$^{19}$ and R$^{20}$ are each independently selected from $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, and substituted $C_2$-$C_6$ alkynyl.

6. The compound of claim 5, wherein R$^{19}$ and R$^{20}$ are each independently selected from methyl, ethyl, propyl, butyl, pentyl and hexyl.

7. The compound of claim 1, wherein R$^{18}$ for each occurrence is independently selected from $C_1$-$C_6$ alkyl, substituted $C_1$-$C_6$ alkyl, bromo, chloro, fluoro, phenyl, substituted phenyl, benzyl, substituted benzyl, $C_1$-$C_6$ alkoxy, $C_1$-$C_6$ perhaloalkyl, and amino.

8. The compound of claim 1, wherein $R^{18}$ for each occurrence is independently selected from hydrogen, $C_1$-$C_4$ alkyl, substituted $C_1$-$C_4$ alkyl, bromo, chloro, fluoro, phenyl, benzyl, $C_1$-$C_4$ alkoxy, $C_1$-$C_4$ haloalkyl, and amino.

9. The compound of claim 8, wherein $R^{18}$ for each occurrence is independently selected from hydrogen, methyl, ethyl, bromo, chloro, fluoro, methoxy, ethoxy and $CF_3$.

10. The compound of claim 9, wherein B and B' are each independently selected from phenyl and substituted phenyl.

11. The compound of claim 10, wherein B and B' are each independently selected from phenyl substituted with one or more groups independently selected from alkoxy, halogen, amino, perhaloalkoxy, acyl, carboxy, and alkoxycarbonyl.

12. The compound of claim 11, wherein B and B' are each independently selected from phenyl substituted with one group selected from $C_1$-$C_4$ alkoxy, fluoro, chloro, and $CF_3$.

13. The compound of claim 12, wherein B and B' are 4-methoxyphenyl.

14. The compound of claim 1 chosen from:
 3,3-bis-(4-methoxyphenyl)-7,12-bistrifluoromethyl-13,13-dimethyl-3H,13H-indeno[2,1-f]naphtho[1,2-b]pyran; and
 3,3-diphenyl-7,12-bistrifluoromethyl-13,13-dimethyl-3H,,13H-indeno[2,1-f]naphtho[1,2-b]pyran.

15. A photochromic composition comprising the compound of claim 1 and optionally at least one other photochromic compound, wherein said composition comprises:
 (a) a single photochromic compound;
 (b) a mixture of photochromic compounds;
 (c) a material comprising at least one photochromic compound;
 (d) a material to which at least one photochromic compound is chemically bonded;
 (e) material (c) or (d) further comprising a coating to substantially prevent contact of the at least one photochromic compound with external materials;
 (f) a photochromic polymer; or
 (g) mixtures thereof.

16. A photochromic composition comprising at least one compound of claim 1 incorporated into at least a portion of an organic material, said organic material being a polymeric material, an oligomeric material, a monomeric material or a mixture or combination thereof.

17. The photochromic composition of claim 16 wherein said polymeric material comprises polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), poly(ethylene terephthalate), polyester, polysulfone, polyolefin, copolymers thereof, and/or mixtures thereof.

18. The photochromic composition of claim 16 wherein the photochromic composition further comprises at least one additive chosen from dyes, antioxidants, kinetic enhancing additives, photoinitiators, thermal initiators, polymerization inhibitors, solvents, light stabilizers, heat stabilizers, mold release agents, rheology control agents, leveling agents, free radical scavengers, and adhesion promoters.

19. A photochromic article comprising a substrate and a photochromic compound according to claim 1 connected to at least a portion of a substrate.

20. The photochromic article of claim 19 comprising an optical element, said optical element being at least one of an ophthalmic element, a display element, a window, and a mirror.

21. The photochromic article of claim 20, wherein the ophthalmic element comprises corrective lenses, non-corrective lenses, contact lenses, intra-ocular lenses, magnifying lenses, protective lenses, or visors.

22. The photochromic article of claim 19 wherein the substrate comprises a polymeric material and the photochromic material is incorporated into at least a portion of the polymeric material.

23. The photochromic article of claim 22 wherein the photochromic material is blended with at least a portion of the polymeric material, bonded to at least a portion of the polymeric material, and/or imbibed into at least a portion of the polymeric material.

24. The photochromic article of claim 19 wherein the photochromic article comprises a coating or film connected to at least a portion of the substrate, said coating or film comprising the photochromic material.

25. The photochromic article of claim 24 wherein said substrate is formed from organic materials, inorganic materials, or combinations thereof.

26. The photochromic article of claim 24 further comprising at least one additional at least partial coating or film chosen from photochromic coatings or films, anti-reflective coatings or films, linearly polarizing coatings or films, transitional coatings or films, primer coatings or films, adhesive coatings or films, reflective coatings or films, antifogging coatings or films, oxygen barrier coatings or films, ultraviolet light absorbing coatings or films, and protective coatings or films.

* * * * *

UNITED STATES PATENT AND TRADEMARK OFFICE
CERTIFICATE OF CORRECTION

PATENT NO. : 8,859,097 B2  
APPLICATION NO. : 13/253188  
DATED : October 14, 2014  
INVENTOR(S) : Anu Chopra Page 1 of 1

It is certified that error appears in the above-identified patent and that said Letters Patent is hereby corrected as shown below:

Title page, Column 2, Item (57) Abstract, Line 6, delete "R17" and insert -- $R^{17}$ --

Signed and Sealed this  
Seventeenth Day of February, 2015

Michelle K. Lee  
*Deputy Director of the United States Patent and Trademark Office*